(12) United States Patent
Habeger, Jr. et al.

(10) Patent No.: US 6,356,846 B1
(45) Date of Patent: Mar. 12, 2002

(54) SYSTEM AND METHOD OF REDUCING MOTION-INDUCED NOISE IN THE OPTICAL DETECTION OF AN ULTRASOUND SIGNAL IN A MOVING BODY OF MATERIAL

(75) Inventors: Charles C. Habeger, Jr., Smyrna; Emmanuel F. LaFond, Atlanta; Pierre Brodeur, Smyrna; Joseph P. Gerhardstein, Decatur, all of GA (US)

(73) Assignee: Institute of Paper Science and Technology, Inc., Atlanta, GA (US)

( * ) Notice: Subject to any disclaimer, the term of this patent is extended or adjusted under 35 U.S.C. 154(b) by 0 days.

(21) Appl. No.: 09/170,508

(22) Filed: Oct. 13, 1998

(51) Int. Cl.$^7$ .............................. G01B 5/28; G10K 11/00
(52) U.S. Cl. .............................. 702/40; 702/103; 73/159
(58) Field of Search ................................ 702/41–43, 81, 702/83, 84, 103, 106, 33–35, 39, 40, 113–115, 142, 182–184, 189, 123–126, 135, 150, 151, 170, 171; 493/37, 480; 73/159, 838; 700/122, 127, 129, 143, 145, 150, 152; 162/198, 263; 250/559.06

(56) References Cited

U.S. PATENT DOCUMENTS

| | | | | |
|---|---|---|---|---|
| 3,612,702 A | * | 10/1971 | Troll | 365/430 |
| 4,622,853 A | * | 11/1986 | Leugers | 73/597 |
| 4,730,492 A | * | 3/1988 | Burk | 73/597 |
| 5,025,665 A | * | 6/1991 | Keyes, IV et al. | 73/597 |
| 5,213,649 A | * | 5/1993 | Sepavich et al. | 156/380.7 |
| 5,814,730 A | * | 9/1998 | Brodeur et al. | 73/597 |
| 5,960,374 A | * | 9/1999 | Lausier | 702/81 |

* cited by examiner

Primary Examiner—Marc S. Hoff
Assistant Examiner—Manuel L. Barbee
(74) Attorney, Agent, or Firm—Finnegan, Henderson, Farabow, Garrett & Dunner, L.L.P.

(57) ABSTRACT

The present invention provides a system and method to reduce motion-induced noise in the detection of ultrasonic signals in a moving sheet or body of material. An ultrasonic signal is generated in a sheet of material and a detection laser beam is moved along the surface of the material. By moving the detection laser in the same direction as the direction of movement of the sheet of material the amount of noise induced in the detection of the ultrasonic signal is reduced. The scanner is moved at approximately the same speed as the moving material. The system and method may be used for many applications, such in a paper making process or steel making process. The detection laser may be directed by a scanner. The movement of the scanner is synchronized with the anticipated arrival of the ultrasonic signal under the scanner. A photodetector may be used to determine when a ultrasonic pulse has been directed to the moving sheet of material so that the scanner may be synchronized the anticipated arrival of the ultrasonic signal.

23 Claims, 7 Drawing Sheets

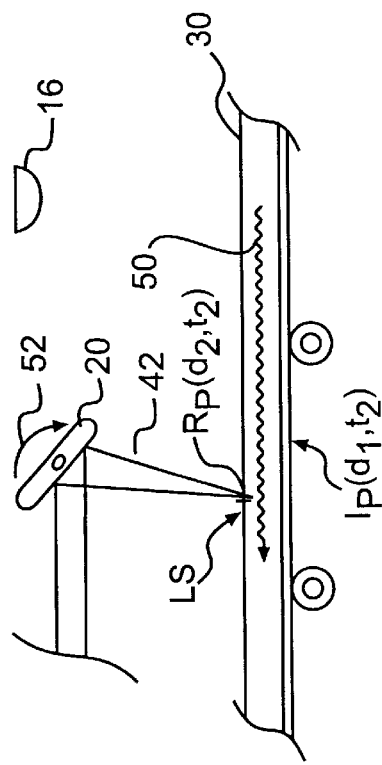
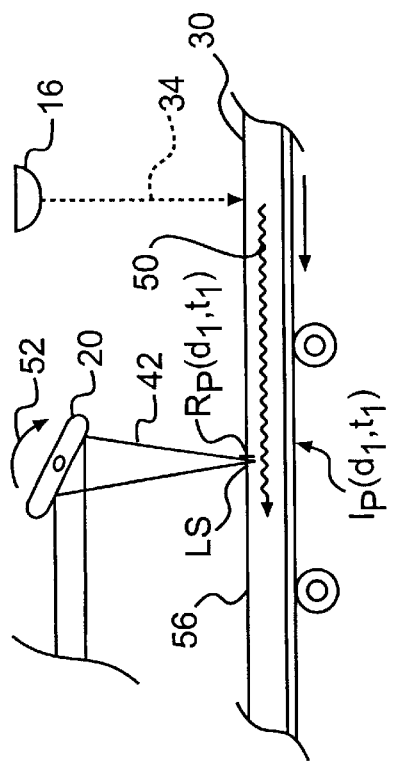
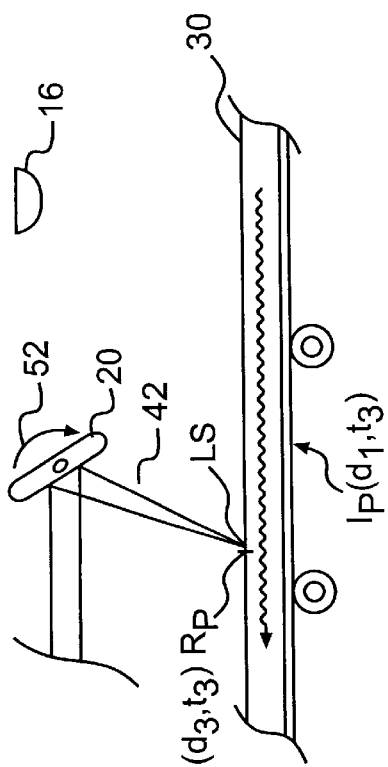

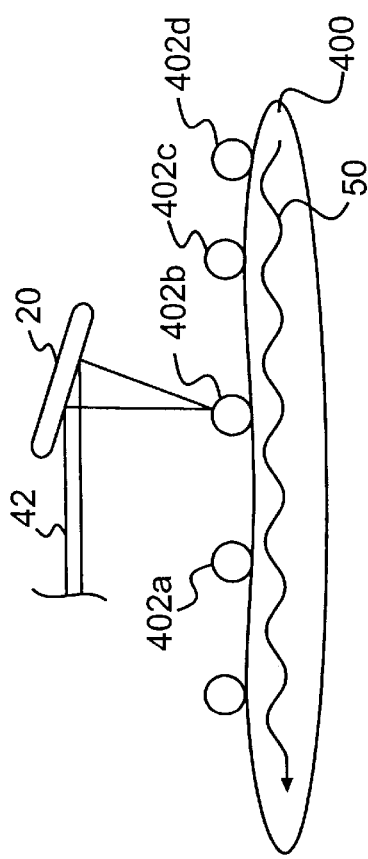
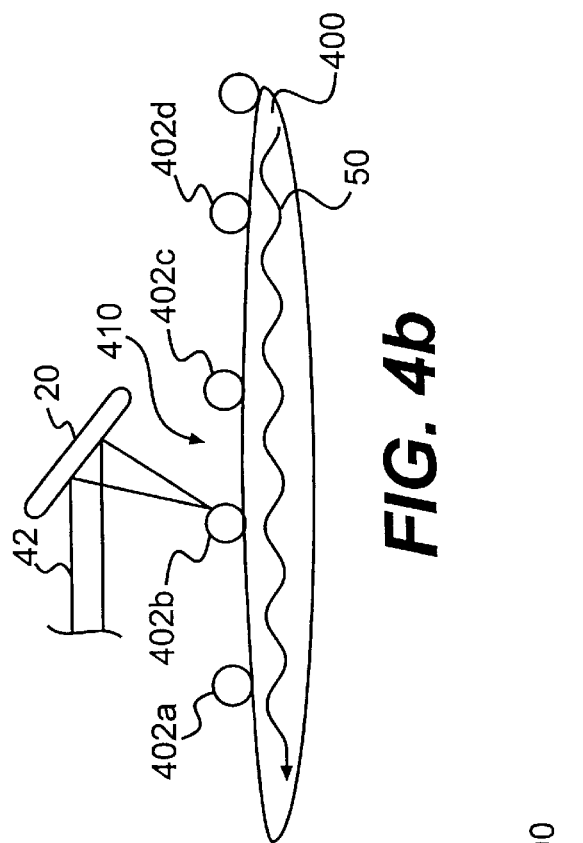
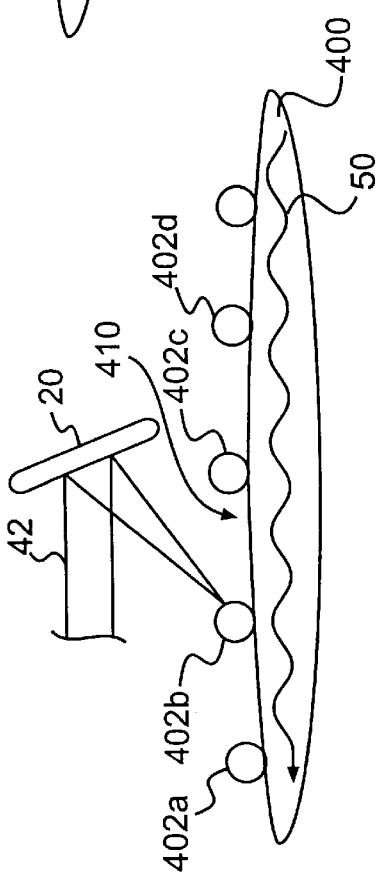
FIG. 4a
FIG. 4b
FIG. 4c

SYSTEM AND METHOD OF REDUCING MOTION-INDUCED NOISE IN THE OPTICAL DETECTION OF AN ULTRASOUND SIGNAL IN A MOVING BODY OF MATERIAL

GOVERNMENT RIGHTS

The government of the United States has rights in this invention pursuant to Contract No. DE-FC07-971D13578 awarded by the U.S. Department of Energy.

FIELD OF THE INVENTION

The present invention relates to measuring the mechanical properties of moving sheet or web-like materials, and more particularly, relates to a system and method for detecting ultrasonic signals, in a non-contact manner, in moving sheet or web-like materials.

BACKGROUND OF THE INVENTION

Ensuring quality control is the goal of most, if not all, manufacturers. In production environments where large quantities of product are produced in a relatively short amount of time, an inefficient quality control process can cause a substantial loss in production time, product, and revenue. Steel and paper production are typically high quantity operations and consequently would benefit from an efficient quality control mechanism. In each of these systems, the steel or paper product is typically produced in a sheet or web-like form along a production line at relatively high speeds. One of the key quality control parameters tested for these materials is strength. Testing the material strength of these products can be accomplished in many ways. Two general types of strength tests are destructive-type tests and non-destructive-type tests.

In destructive-type tests, the material is sampled and tests are conducted off-line to determine the various properties. Test time for off-line testing is relatively long, resulting in delays between sample collection and process changes. This delay allows substantial amounts of sub-standard material to be produced. Non-destructive tests, on the other hand, can often be performed on-line while the web or sheet-type material is being produced. One type of non-destructive testing used for web-like materials is ultrasonic testing. Ultrasonic testing is performed on-line enabling a continuous test of the mechanical properties of the material. In ultrasonic testing, sound waves are propagated through the material to determine the velocity of the sound waves. The velocity of the sound waves through the material correlates with the strength of the material.

In non-contact ultrasonic testing, an ultrasonic pulse is induced into the material and a stationery detection laser or interferometer is reflected onto the surface of the material to measure vibrations in the material due to the ultrasonic pulse. Laser interferometers detect surface motion of the material caused by the ultrasonic wave. The detection is normally accomplished by reflecting a laser beam from the surface of the material. The reflected beam is phase-shifted by variations in surface displacement from which desired measurements may be obtained by interfering with a stable "reference" beam. Surface variations may be caused by the ultrasonic wave or by other means, such as mechanical vibrations due to machinery, etc. Thus, the source of variations needs to be distinguished. The frequency component of the mechanical vibrations are usually in the 1–1000 Hz range whereas the frequency component of the ultrasonic signals are typically in the 1 MHz (megahertz) range. The different frequencies of the vibrations and the sought-after ultrasonic signals enable the machine vibrations to be easily filtered out so that the detection of the ultrasonic signal is readily obtained.

While mechanical vibrations may be easily filtered, noise induced by the texture of the surface can be problematic depending on the type of material being tested and/or on the speed at which the material passes under the detection laser beam. Non-contact testing has been successfully performed using a stationary laser beam in the production of steel sheets moving along a conveyor. The success of laser detection of ultrasonic sound in the production of steel can be attributed to the relatively slow moving speed of the steel on a conveyor and to the relatively smooth texture of steel. However, using on-line, non-contact measurements of ultrasound wave velocities in paper production is more problematic because the paper moves at a much higher speed and is more fibrous than steel. The high speed of production and very fibrous nature of the paper's texture causes detection problems for a detection laser.

When a light from a stationery laser is reflected from a moving textured surface, such as paper, additional phase changes in the signal result from the textured surface. Specifically, the laser beam reflects on a fiber at one instance and, at the next instance, the laser beam reflects into the "valley" between fibers and, at the next instant, reflects again at the top of another fiber. The undulating laser beam reflection caused by the "hills" and "valleys" of the paper texture produces a wave of noise that needs to be filtered out in order to detect the ultrasonic waves. However, filtering texture noise is not an option in fast moving materials because the frequency of the moving material can produce a noise component or texture signal that is in the 1 MHz range. The 1 MHz frequency range of the texture noise makes distinguishing the ultrasound wave virtually impossible because the ultrasound wave propagates at the same frequency. Additionally, the amplitude of the ultrasound wave is less than 0.1 micron whereas the amplitude due to surface deformation caused by the fibers of paper are approximately ten microns. Thus, not only does the frequency interfere with the filtering of the ultrasonic wave from the texture noise, but the texture noise blocks out the smaller ultrasonic signal.

Therefore, there is a need in the art for a non-contact ultrasonic testing system that is operative to distinguish ultrasonic signals from texture noise for relatively fast moving surfaces. In such a system, a need exists to reduce or eliminate motion-induced noise caused by the texture of a moving surface.

SUMMARY OF THE INVENTION

Generally described, the present invention provides a method to reduce motion-induced noise in the optical detection of ultrasonic signals in a moving sheet or body of material. The system of the present invention uses a detection laser to detect the ultrasonic signals traveling in the sheet of material.

More particularly, the present invention provides a method of reducing noise in the detection of an ultrasonic signal in a moving body of material by moving a detection laser beam along the surface of the material in the same direction as the direction of movement of the sheet of material. By moving the laser as described, the amount of textural noise induced in the detection of the ultrasonic signal is reduced. The method of the present invention may be used for many applications, such as in paper, steel or plastic making processes.

Another embodiment of the present invention includes a system for detecting ultrasonic signals in a moving body of material. In this system, a body of material moves in a certain direction along a defined path. An ultrasound generator directs an ultrasonic signal into the moving body of material. A scanner directs a laser beam onto the surface of the moving body and moves the laser beam along the surface of the moving body in the direction of movement of the moving body. A detection device detects a reflection of the laser beam from the surface of the moving body to detect the movement of the ultrasound signals in the moving body.

The scanner is preferably operable to move the laser beam at a speed that is approximately at the speed of the moving body. The scanner may be a galvanometer that is rotatable in the direction of movement of the moving body or may be any type of scanner suitable for directing the laser beam along the surface of the moving material. The operation of the scanner may be synchronized to begin when the ultrasonic signal is expected to arrive in the scanning path of the scanner.

Preferably, a photodetector is used to synchronize the movement of the scanner with the generation of the ultrasonic pulse. The photodetector detects the generation of a pulse from the ultrasound generator and generates a start timer signal. A timing circuit controls the movement of the scanner in response to receiving the start timer signal. The detection laser beam scans the body in the direction of movement, at a speed near that of the body, over a time period sufficient to detect the ultrasound pulse. The moving body of material may be a web of paper, steel, or other sheet material.

Thus, it is an object of the present invention to provide a method and system for improving the optical detection of ultrasonic signals in a moving body of material.

It is another object of the present invention to reduce the amount of texture-induced noise generated in the detection of ultrasonic signals in a moving body of material.

These and other objects will be readily apparent to those skilled in the art upon reviewing the accompanying descriptions and figures.

BRIEF DESCRIPTION OF THE DRAWINGS

FIGS. 2a, 2b, and 2c are diagrams of the movement of a scanner in accordance with the principles of the present invention.

FIGS. 4a, 4b, and 4c are diagrams that show the manner in which motion-induced noise is reduced by use of the method or system of the present invention.

DETAILED DESCRIPTION OF THE INVENTION

A detailed description of the preferred embodiment of the present invention is provided in connection with the accompanying figures. A system or method operating in accordance with the preferred embodiment of the present invention reduces motion-induced noise via a non-contact method of detecting ultrasonic signals in a moving body of material. Non-contact generally means that a mechanical detection device, such as a device containing a transducer, does not physically contact the material being tested for ultrasonic signals. The noise, which is reduced, is primarily induced by undulations detected in the texture of the surface of the moving material. The present invention helps to reduce noise in the detection of ultrasonic signals in a moving material or surface by reducing the apparent speed of the surface of the moving material with respect to a detection laser. The apparent speed of the surface of the moving material is reduced by using a scanner to move a laser beam along the surface of the moving body in the direction of motion of the moving body. Preferably, the speed of the scanning equals the speed of the moving material. By reducing the apparent speed of the moving body with respect to the detection laser, fewer texture deformations on the surface are encountered by the detection laser and noise induced by the passing of texture deformations under the laser beam is consequently reduced or shifted to lower frequencies. The reduction of texture deformations detected by the laser beam enables the ultrasonic signal to be more easily and accurately detected. Another benefit of scanning or moving the laser beam, as discussed herein, is that the doppler shift from the ultrasound wave velocities would be removed.

Figure 1:
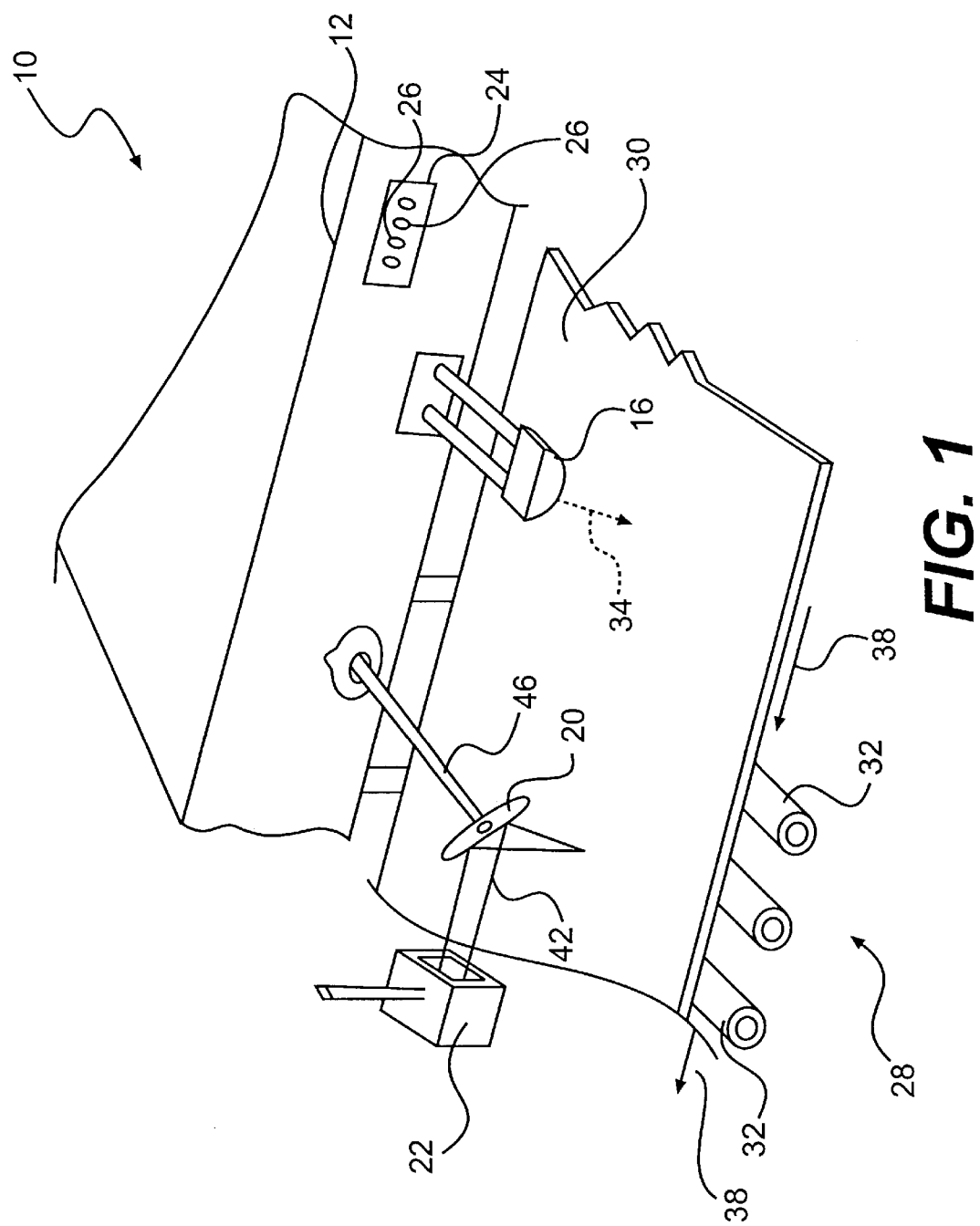
FIG. 1 is a perspective view of a system constructed in accordance with the principles of the present invention.

Referring to FIG. 1, a motion-induced noise reduction system 10 constructed in accordance with the teachings of the present invention is illustrated. It should be appreciated that the motion-induced noise reduction system 10 may be used in various production environments, such as paper mills and steel mills. The system 10 is a non-destructive, non-contact, physical property testing system suited for on-line testing of moving sheet or web-like materials. A control machine 12 controls various subsystems of the present invention. The subsystems may include an ultrasound generator 16, a scanner 20, a detection system 22 and a conveyor system 28. These subsystems may be controlled by operation of a control panel 24 having controls 26. By operating the subsystem components according to the principles of the present invention, various properties, such as the stiffness of a moving material 30, can be determined. The moving material 30 may be transported along a defined path by rollers 32. It should be appreciated that the moving material may be transported by a moving wire mesh or grid, conveyor belt or other means known to those skilled in the art. The moving material 30, for example, may be any form of sheet material such as paper, steel, plastic, etc.

The ultrasound generator 16 generates an ultrasonic pulse 34 into the moving material 30 for detection by the detection system 22. The ultrasonic signals travel through the moving material 30 in the direction of the movement of the material as indicated by the arrows 38. A detection laser beam 42 is generated from the detection system 22 to the surface of the moving material and is reflected from the surface for analysis by the detection system 22. The detection system 22 preferably detects the ultrasonic signal in a standard way by mixing the reflected signal with a reference beam. The laser beam 42 is preferably generated by a laser interferometer. The detection system 22 may be any type of suitable detection system known by those skilled in the art, such as a photo refractive system, a Fabry-Perot system, a photo EMF system, a vibrometer, a Michelson interferometer, a Mach-Zehnder interferometer, or a self-mixing system.

As indicated above, the scanner 20 moves the laser beam along the surface of the moving material 30, in the same direction of the moving material 30, to reduce motion-induced texture noise. Additionally, the scanner collects backscattered light and directs the light back to the detection system. Many types of scanners may be chosen for implementation with a system operating according to the present invention, such as galvanometer, rotating prism, taut-band (resonant), piezoelectric, or acousto-optic scanner. The scanner 20 is preferably a galvanometer that is rotatable about an axis 46. The speed of movement of the scanner 20 is coordinated with the speed of the moving material and lasts for the duration of the ultrasonic signals. At normal production speeds, the scanner 20 of the present invention reduces the surface deformations detected by the detection system as compared to static or stationery laser detection systems, which would detect surface variations in a frequency range near 1.0 MHz. This frequency range is near the frequency of the ultrasonic signals which prevents static laser detection systems from being effective in distinguishing the ultrasonic signals produced by an ultrasonic generator from surface variations. Additionally, the depth of the surface variations can cause noise to be produced at an amplitude higher than the amplitude of the ultrasonic signals, thereby potentially masking the ultrasonic signal. When the scanner 20 scans the laser beam 42, the laser beam 42 may go in and out of focus on the sample or moving material 30. The focus problem can be overcome by using a parabolic mirror or lens (such as a gradient index lens). The moving detection laser beam 42 or scanner 20 of the present invention reduces or eliminates these texture-induced detection problems to provide an improved non-contact ultrasonic wave detection system.

Referring to FIGS. 2a, 2b, and 2c, the operation of a motion-induced noise reduction system 10 is illustrated. Referring first to FIG. 2a, the initial function that occurs when the scanning and detection begins is illustrated. When the ultrasound generator 16 generates an ultrasonic pulse 34, the movement of the scanner 20 and the generation of the detection laser beam 42 are synchronized to coincide with the passage of an ultrasonic signal 50 produced in the moving material 30. That is, the forward scan of the scanner 20 will be synchronized to start with the projected arrival of the ultrasonic signal 50 at the initial laser detection point of the path of the scanner and will continue scanning until the signal has past the scanning range. The scanner 20 is rotated at a rate that corresponds to the speed of the moving material 30. The direction of rotation is indicated by the arrow 52.

By matching the scan rate of the laser beam, via the scanner 20, to the speed of the moving material for the duration of scan, the laser illuminated spot, LS, will effectively remain static with respect to the reference point, $R_p$, on the moving material. Rotating the scanner 20 at an angular velocity that corresponds to the velocity of the moving material 30 enables the detection laser beam 42 to experience very few, if any, texture variations at the optimum scan rate. The optimum scan rate is the scan rate that equals the speed of the moving material 30. The initial static position, $I_p$, with respect to the stationary components of the system, illustrates the position that would be the non-moving laser reference point in a static laser detection system. The reference point $R_p$ may be defined as having a distance coordinate d, with respect to the point $I_p$ and a time coordinate of t. The $t_1$ coordinate indicates the time at which the detection laser beam 42 initially illuminated the surface. The initial laser detection distance is $d_1$. As the scanning process proceeds, the distance d will become larger.

Referring to FIG. 2b, the scanner 20 is shown rotated a certain number of degrees in the clockwise direction to move the detection laser beam 42 in the leftward direction to correspond to the motion of the moving material 30. As illustrated in FIG. 2b, the detection laser beam 42 still reflects approximately at the initial reference point $R_p$ because the velocity of the scanner 20 is synchronized with the speed or velocity of the moving material 30. The reference point $R_p$ of FIG. 2b may be now defined by the coordinates $(d_2, t_2)$. The distance $d_2$ represents the distance between the reference point $R_p$ and the initial static point of reference $I_p$. This distance measurement $d_2$ was taken at the time $t_2$. It should be appreciated that the detection laser beam 42 continuously measures surface variations due to the ultrasonic signal for the duration of the scan. The best measurements of the ultrasonic signal occur when the speed of scanner 20 reaches the speed of the moving material 30.

Referring to FIG. 2c, the scanner 20 is shown rotated at a farther distance than the rotation distance indicated in FIG. 2b. As illustrated, the detection laser beam 42 still tracks the movement of the reference point $R_p$ to reduce the apparent speed of the moving material 30 with respect to the detection laser beam 42. By reducing the apparent speed of the surface of the moving material 30 with respect to the detection laser beam 42 of the detection system 22, fewer textural disturbances are encountered by the detection laser beam 42. Therefore, the signal to noise ratio and the detection of the ultrasound signal is substantially improved over static laser detection systems. It should be appreciated by those skilled in the art that the angular relationships of the laser beam with respect to the scanner and moving material 30 are somewhat exaggerated in FIGS. 2a, 2b and 2c to clearly indicate the principles of the present invention. In the preferred embodiment of the present invention, ultrasonic detection scans are intermittently or periodically made at selected intervals to meet the quality control specifications of the production operation.

Figure 3A:
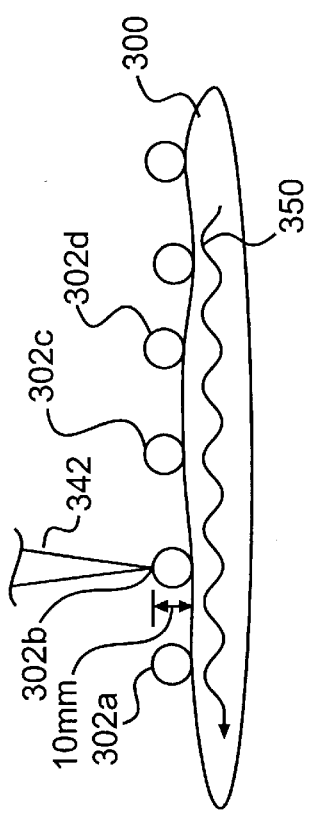
FIGS. 3a, 3b, and 3c are diagrams that show the manner in which motion-induced noise is produced in a static laser detection system.
Figure 3B:
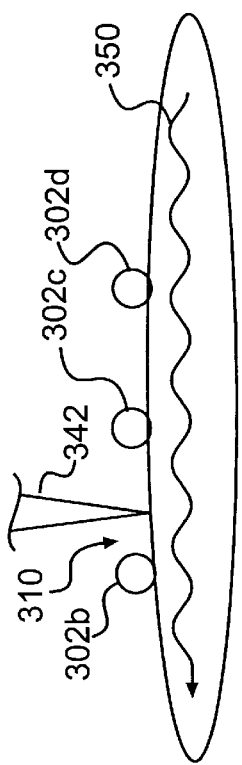
Figure 3C:
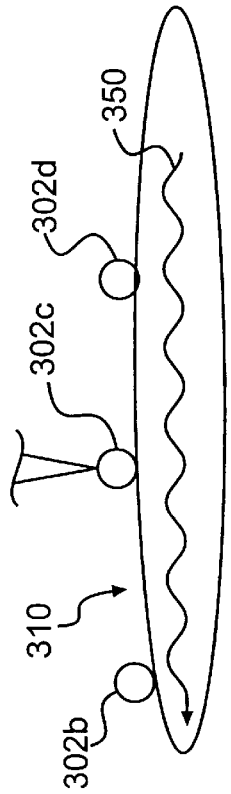

Referring to FIGS. 3a, 3b, and 3c, an example of the noise that would be induced in a fixed laser beam detection system is illustrated. In FIG. 3a, various fibers 302a–d, generally referred to as 302, of a web 300 of paper are illustrated. The fibers 302 are approximately 10 microns in diameter. It should be appreciated by those skilled in the art that the size of the fibers of a web may vary. When the fixed laser beam 342 is directed toward the moving web 300, the laser beam strikes the fiber 302b. As the web 300 progresses along its path (FIG. 3b), the laser beam 342 is directed into the gap 310 between the fibers 302b and 302c. The distance of vertical displacement of the laser beam 342 from the top of the fiber 302b to the bottom of the gap 310 is approximately 10 microns. This displacement is measured by the detection system associated with the laser beam. Referring to FIG. 3c, the laser beam is then deflected up 10 microns when the fiber 302c moves into the path of the beam. The amplitude of the upward deflection of the laser beam 342 is also approximately 10 microns. The amplitude of surface deformation from an ultrasonic wave 350 is less than 0.1 micron. Therefore, the deflection of the laser beam 342 with respect to the fibers 302 of the web material is much greater than the deformation caused by the ultrasonic wave 350 which makes it difficult to detect the deformations due to the ultrasonic wave 350. The surface variations due to the ultrasonic wave 350 are particularly more difficult to detect when the fibers move at 10–35 meters per second producing a signal frequency that is in the same range as the frequency of the ultrasonic signal. Therefore, it becomes virtually impossible to detect the deformations due to the ultrasonic wave because the frequency of the texture noise is approximately the same as the frequency of the ultrasonic sound. Furthermore, the detection of amplitude variations will be dominated by the greater amplitude variations caused by the dimensions of the fiber.

Referring to FIGS. 4a, 4b and 4c, a more detailed view of the manner in which the scanner 20 of the present invention helps to eliminate texture noise is illustrated. As discussed above, texture noise is eliminated by moving the scanning laser beam in the direction of movement of the moving material to reduce the number of surface level variations encountered by a detection laser. Referring first to FIG. 4a, when the detection laser beam 42 is projected onto the web 400, the detection laser beam 42 projects onto a fiber 402b. Although the laser beam 42 is shown projected onto a single fiber, an actual detection laser will illuminate a spot that is approximately 1 millimeter in diameter, which will cover several fibers. The illustrations in the figures are shown in a simple manner to clearly convey the principles of the present invention. By operating according to principals of the invention, the movement of the scanner 20 (FIG. 4b), at the speed of the moving web 400, causes the detection laser beam 42 to track the movement of the initial point of reference, the fiber 402b. Because the detection laser beam 42 tracks the location of the initial area of contact or fiber, upon which the detection laser beam 42 was initially projected, texture variations due to the gap 410 and the fiber 402c are not encountered by the detection laser beam 42. Therefore, noise due to the displacement of the detection laser beam 42 caused by deformations in the surface are minimized. FIG. 4c shows a further progression of the tracking or scanning of the detection laser beam 42 along the surface of the moving web 400 at the fiber 402b. In view of the stable detection point of the laser beam 42 with respect to the web 400 or, particularly, the fiber 402b, the detection system 22 (FIG. 1) may more easily detect variations in the reflection of the detection laser beam due to the ultrasonic signal 50 traveling through the web 400. The signal to noise ratio is substantially improved as compared to the static laser detection system discussed in connection with FIGS. 3a, 3b, and 3c.

Figure 5:
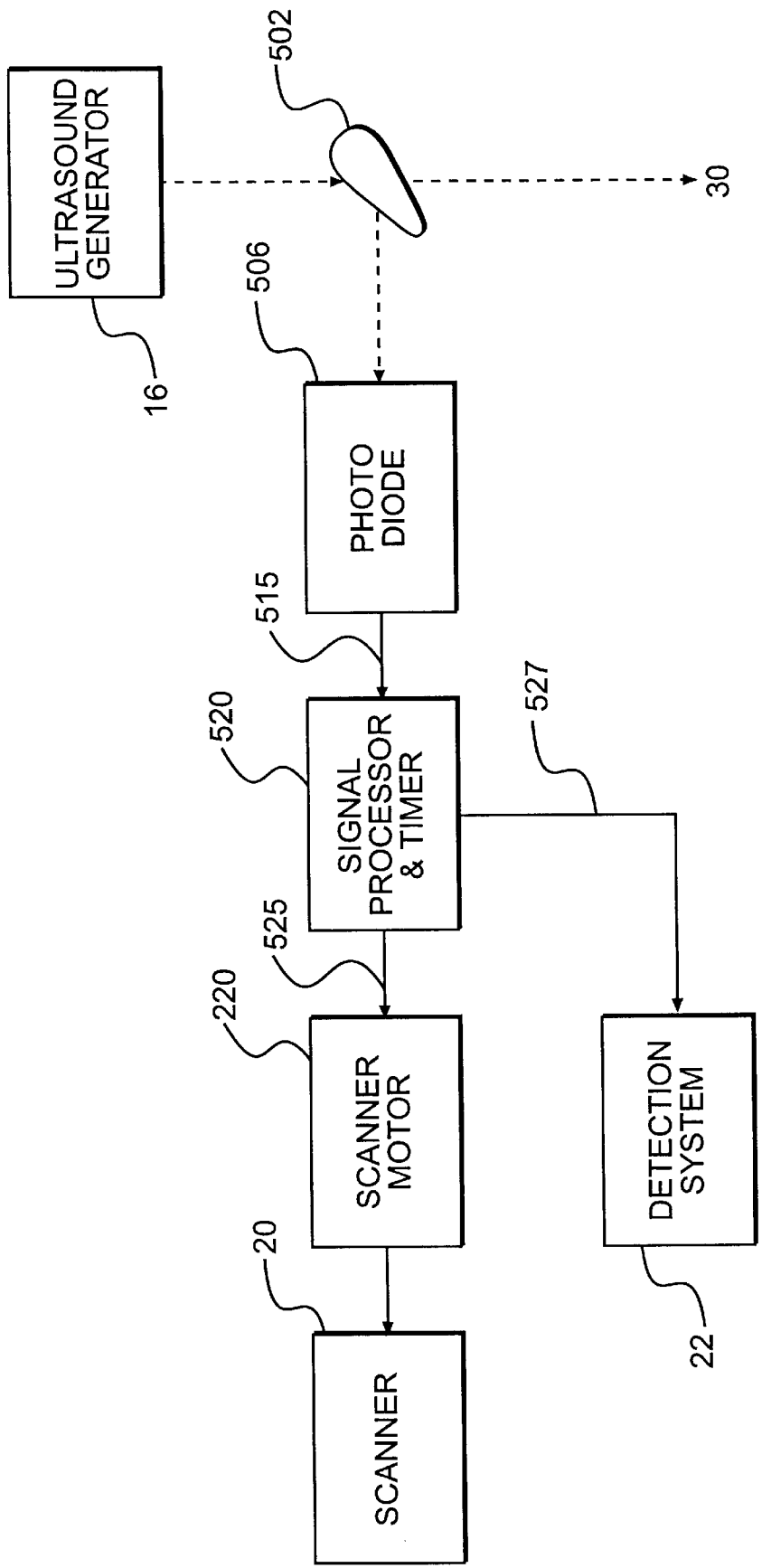
FIG. 5 is a diagram of the components used to synchronize the movement of the scanner with the arrival of an ultrasonic pulse in the path of the scanner.

Referring to FIG. 5, a block diagram of the components for synchronizing the detection system 22 and scanner 20 with the ultrasonic pulse 34 (FIG. 2a) and signal 50 (FIG. 2a) is illustrated. When the ultrasonic generator 16 generates an ultrasonic pulse 34, a partially reflecting mirror 502 reflects a portion of the detection laser beam 42 (FIG. 1) and allows the unreflected portion to pass through the partially reflecting mirror 502. The unreflected portion of the ultrasonic pulse proceeds through the partially reflecting mirror 502 to the moving material 30, as discussed above. When the ultrasonic pulse 34 is generated, the partially reflecting mirror 502 deflects a 1/10 of 1% of the ultrasonic laser pulse to a photodetector or photodiode 506. When the photodiode 506 detects the generation of the ultrasonic pulse 34, a signal 515 is generated to the signal processor and timer 520. The signal 515 causes the signal processor and timer 520 to synchronize the scanner 20 and detection system 22 with the projected arrival of the ultrasonic signal at the scan location for the moving material. When the signal 515 is received at the signal processor and timer 520, a timer times a predetermined time that is calculated based on the speed of the moving material 30, the size and weight of the scanner, and distance of the scanner from the surface of the moving material 30. When the time period expires, the signal processor and timer 520 generates a signal 525 to the scanner motor 220 to cause the scanner 20 to rotate or move in the direction of the moving material 30 to synchronize the scanner movement with the movement of the moving material 30. The signal processor and timer 520 also generates a signal 527 to the detection system 22 to initiate the operation of the laser beam 42. The command signal 525 to the scanner 20 is a time-varying voltage. A control loop can be used to keep the angular position of the scanner 20 proportional to the instantaneous voltage of the command signal (the proportionality constant is x degrees/volt).

The method of generating the ultrasonic pulse discussed in connection with FIG. 5 is a pulsed laser. The pulsed laser has a short width (typically 1–20 microseconds) and sends a burst of light to the sample to excite ultrasound waves in the moving material via thermoelastic, ablation or plasma generation phenomenon. Other types of non-contact ultrasound generators that can be used in connection with the present invention are air-coupled piezoelectric transducers. Air-coupled piezoelectric transducers send an ultrasound wave through the air to the surface of the sample. When an air-coupled transducer is used, an electronic signal may be generated from the device to indicate the generation of an ultrasonic pulse. The electronic signal can be used to synchronize the detection laser 42 and detection system 22 as discussed herein. In an alternative embodiment of the synchronization aspects discussed in connection with FIG. 5, an electronic synchronization signal can generated from electronics associated with the ultrasonic generator 34 to be used for synchronizing the detection laser 42 and the detection system 22, instead of detecting the optical pulse for use in synchronization.

Figure 6A:
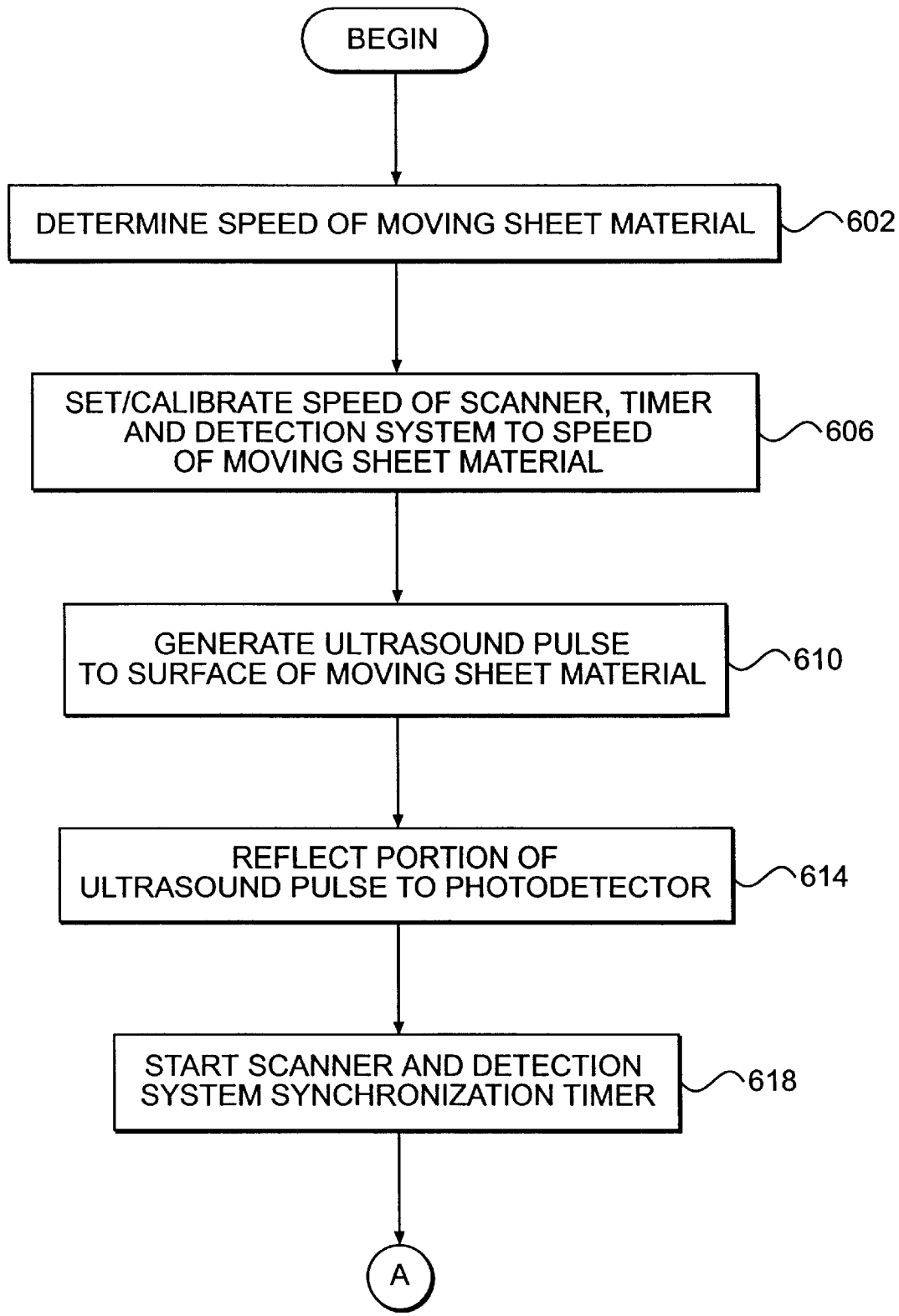
FIGS. 6a and 6b are flow diagrams that illustrate the processes of the present invention.
Figure 6B:
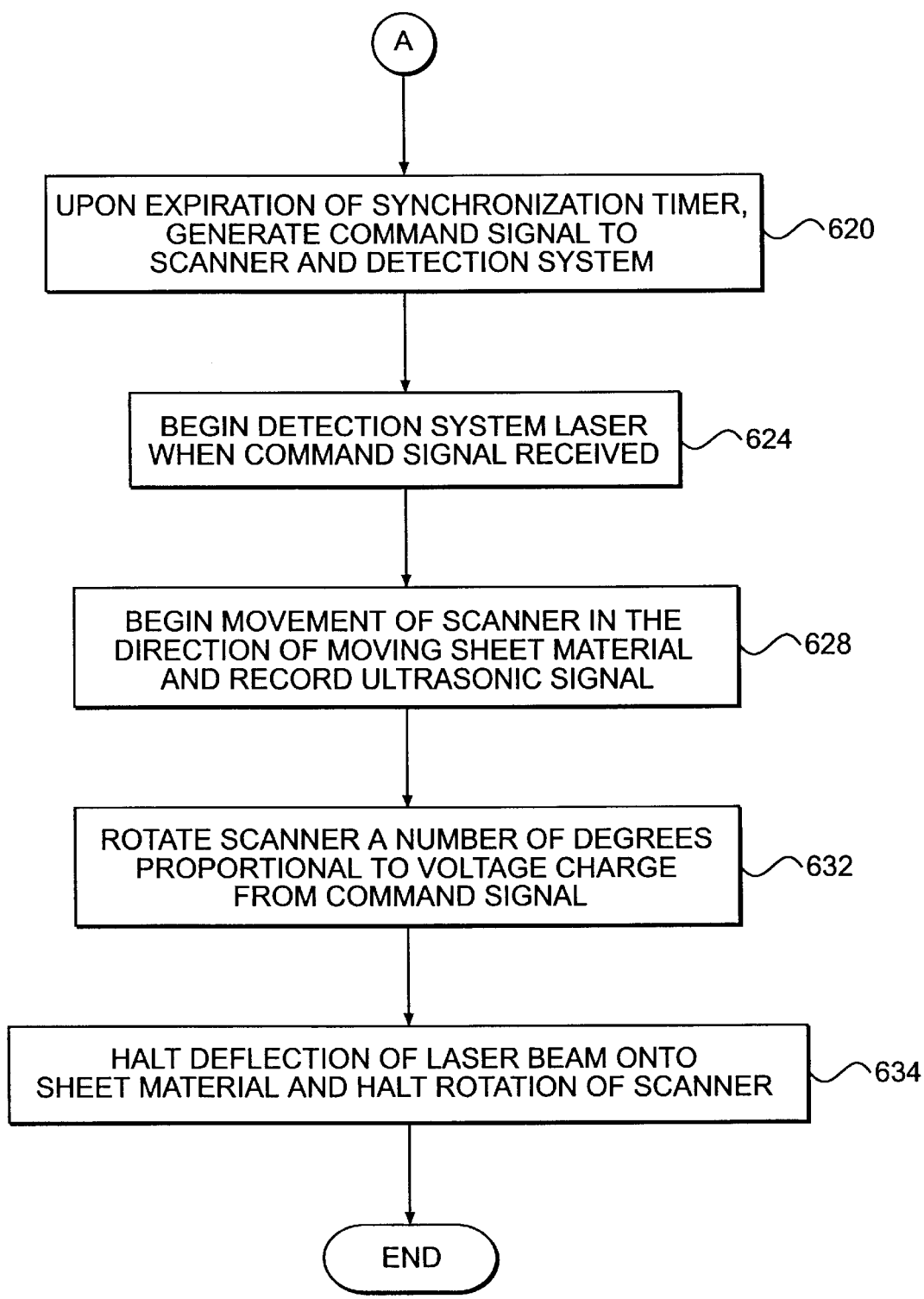

The steps implemented in the preferred embodiment of the present invention are discussed in connection with FIGS. 1, 2a, 2b, 2c, 5, 6a and 6b. Referring to FIGS. 6a and 6b, the steps implemented for scanning a detection laser in the direction of and along the surface of a moving sheet material are discussed. The speed of the moving web may be determined by using an external tachometer input. Also the web speed may be determined by evaluating the texture noise of the material when ultrasound waves are not traveling under the detection report to known predetermined noise measurements. At step 602, the speed of the moving material 30 is determined. The speed of the moving material 30 is determined in order to synchronize the movement of the scanner 20 and the detection laser beam 42 with the movement of the moving material 30 along its conveyor. The speed of the moving web may be determined by using an external tachometer input. Also, the web speed may be determined by evaluating the texture noise of the moving material, with the detection system 22, when ultrasound waves are not traveling under the detection spot. These detected texture noise levels can then be compared, using a table or algorithm, to predetermined texture noise levels (frequency and/or amplitude) that have been associated with certain web speeds to determine the speed of the web. At step 606, after the speed of the moving material 30 is determined, the speed of the scanner 20, timer 520 and detection system 22 are calibrated to ensure synchronization of operation. After the system 10 has been calibrated, the system 10 is prepared to evaluate the properties of the moving material using the non-contact ultrasound detection method discussed herein. At step 610, the ultrasound generator 16 causes an ultrasonic pulse 34 to be generated in the moving material 30. At step 614, a portion of the ultrasonic pulse 34 is reflected to a photodetector or photodiode 506. The photodiode 506 provides a signal that enables the scanning and detection operations to be synchronized with the ultrasonic pulse moving through the moving material 30. At step 618, the synchronization timer 520 is started. The time period timed by the synchronization timer varies according to the speed of the moving material, size of the scanner, and the distance of the scanner from the moving material and other parameters as known to those skilled in the art.

The process then proceeds to step 620 where upon expiration of the synchronization timer 520, a command signal is generated to the scanner 20 and the detection system 22. This command signal provides a start signal and serves as a synchronization pulse for synchronizing the detection system and the scanner with the ultrasonic pulse traveling through the moving material 30. At step 624, the detection system is started when the command system is received and at step 628, the movement of a scanner is initiated in the direction of the moving material 30. It should be appreciated that steps 624 and 628 occur virtually simultaneously. As indicated at step 632, the scanner 20 is rotated a number of degrees proportional to the voltage from the command signal as described herein above. At step 634, the rotation of the scanner and deflection of the laser beam onto the moving material 30 are stopped. The scanning and detection process may be intermittently or periodically repeated to test the quality of the moving material.

The descriptions given herein are provided as examples and are not intended to limit the principles or scope of the present invention. Those skilled in the art would readily appreciate from a review of the descriptions herein that many modifications, changes or extensions may be made from the specific embodiment described herein without departing from the scope of the invention defined by the following claims.

What is claimed:

1. A system for improving the detection of ultrasound signals in a moving body of material, comprising:
    a scanner for directing a laser beam onto the surface of a moving body of material, the scanner moving the laser beam along the surface of the moving body in the direction of movement of the moving body; and
    a detection device for detecting a reflection of the laser beam from the surface of the moving body to detect the movement of an ultrasound signal in the moving body.

2. The system of claim 1 wherein the scanner is operable to move the laser beam at a speed that is at or near the speed of the moving body.

3. The system of claim 1 wherein the scanner is a galvanometer that is rotatable in the direction of movement of the moving body.

4. The system of claim 1 wherein the operation of the scanner is synchronized to begin when the ultrasound signal is expected to arrive in the area to be scanned on the moving body.

5. The system of claim 4 wherein the operation of the scanner ends after the ultrasonic signal passes the location of the area that is scanned by the scanner.

6. The system of claim 4 further comprising a signal detector for detecting a generated signal indicative of the generation of an ultrasonic pulse and for generating a start timer signal in response to detection of the generated signal; and
    a timer for synchronizing movement of the scanner with the moving body in response to receiving the start timer signal.

7. The system of claim 6 wherein said signal detector is a photodetector for detecting the generation of a laser pulse to initiate an ultrasound signal in the moving body.

8. The system of claim 7 wherein the timer times a predetermined time period in response to receiving the start timer signal and the timer generates a start scanner signal to the scanner for causing the scanner to move the laser beam along the moving body in the direction of movement of the moving body.

9. The system of claim 7 wherein the photodetector is a photodiode.

10. The system of claim 1 wherein the moving body of material is a web of paper and moves along a defined path of a paper making machine.

11. The system of claim 1 wherein the amount of movement of the scanner is calibrated to be directly proportional to the shape of a voltage curve from a command signal generated to the scanner to power the scanner.

12. The system of claim 1 wherein the detection device is a laser interferometer.

13. The system of claim 12 wherein the laser interferometer generates the laser beam.

14. The system of claim 1 comprising an ultrasound generator for generating an ultrasound signal into the moving body of material.

15. The system of claim 1 wherein said scanner collects reflected light of the laser beam from the moving body and directs the reflected light to the detection device.

16. A method of improving the detection of an ultrasonic signal in a moving body of material, comprising the steps of:
    generating an ultrasonic pulse in a moving body of material;
    projecting a detection laser beam on the moving body of material;
    moving the detection laser beam along the moving body of material in the direction of movement of the moving body of material; and
    detecting the movement of the ultrasonic pulse in the body of material by analyzing a reflection of the detection laser beam from the surface of the moving body of material.

17. The method of claim 16 wherein the step of moving the detection laser beam comprises moving the detection laser beam approximately at the same speed of the movement of the moving body.

18. The method of claim 17 further comprising the step of synchronizing the beginning of movement the detection laser beam with the expected arrival time of ultrasonic signals under the scanner.

19. The method of claim 18 wherein the step of synchronizing further comprises:
    detecting the initiation of the ultrasonic pulse with a photodetector and starting a timer when the initiation is detected; and
    synchronizing the movement of the scanner when a time period timed by the timer expires.

20. A method of improving the detection of an ultrasonic signal in a moving body of material, comprising the steps of:
    generating an ultrasonic signal in a moving body of material; and
    moving a detection laser beam along the surface of the material in the same direction as the direction of movement of the moving body of material to increase signal to noise ratio in the detection of the ultrasonic signal.

21. The method of claim 20 wherein the step of moving comprises moving the detection laser along a web of paper.

22. The method of claim 21 wherein the laser beam is detected by a laser interferometer.

23. A system for improving the detection of ultrasound signals in a moving body of material, comprising:

a scanner for directing a detection beam onto the surface of a moving body of material, the scanner moving the detection beam along the surface of the moving body in the direction of movement of the moving body; and a detection device for detecting a reflection of the detection beam from the surface of the moving body to detect a predetermined type of signal moving in the moving body.

* * * * *

UNITED STATES PATENT AND TRADEMARK OFFICE
CERTIFICATE OF CORRECTION

PATENT NO. : 6,356,846 B1　　　　　　　　　　　　　　　　　　　　　　Page 1 of 1
DATED : March 12, 2002
INVENTOR(S) : Charles C. Habeger, Jr. et al.

It is certified that error appears in the above-identified patent and that said Letters Patent is hereby corrected as shown below:

<u>Title page,</u>
Item [57], ABSTRACT,
Line 17, "synchronized the" should read -- synchronized with the --.

<u>Column 10,</u>
Line 44, "movement the" should read -- movement of the --.

Signed and Sealed this

Twenty-eighth Day of May, 2002

*Attest:*

JAMES E. ROGAN
*Attesting Officer*　　　　*Director of the United States Patent and Trademark Office*